(12) United States Patent
Dye et al.

(10) Patent No.: US 9,533,170 B2
(45) Date of Patent: Jan. 3, 2017

(54) MULTICOLOR LIGHT EMITTING DIODE TREATMENT SYSTEM WITH UNIFORM ILLUMINATION

(71) Applicants: Catherine L. Dye, Los Alamos, NM (US); Markus P. Hehlen, Los Alamos, NM (US)

(72) Inventors: Catherine L. Dye, Los Alamos, NM (US); Markus P. Hehlen, Los Alamos, NM (US)

( * ) Notice: Subject to any disclaimer, the term of this patent is extended or adjusted under 35 U.S.C. 154(b) by 269 days.

(21) Appl. No.: 14/580,430

(22) Filed: Dec. 23, 2014

(65) Prior Publication Data
US 2016/0175609 A1   Jun. 23, 2016

(51) Int. Cl.
*A61N 5/06* (2006.01)
(52) U.S. Cl.
CPC ..... *A61N 5/0616* (2013.01); *A61N 2005/0629* (2013.01); *A61N 2005/0633* (2013.01); *A61N 2005/0642* (2013.01); *A61N 2005/0652* (2013.01); *A61N 2005/0663* (2013.01); *A61N 2005/0665* (2013.01)
(58) Field of Classification Search
CPC .............. A61N 2005/0629; A61N 2005/0633; A61N 2005/0652; A61N 2005/0663; A61N 2005/0642; A61N 5/0616
See application file for complete search history.

(56) References Cited

U.S. PATENT DOCUMENTS

| | | | |
|---|---|---|---|
| 5,876,107 A | 3/1999 | Parker et al. | |
| 6,488,698 B1 | 12/2002 | Hyman | |
| 6,896,693 B2 | 5/2005 | Sullivan | |
| 6,991,644 B2 | 1/2006 | Spooner et al. | |
| 7,077,544 B2 | 7/2006 | Parker | |
| 7,131,990 B2 | 11/2006 | Bansal et al. | |
| 7,438,719 B2 | 10/2008 | Chung et al. | |
| 8,069,857 B2 | 12/2011 | Chung et al. | |
| 8,070,669 B2 | 12/2011 | Brunelle et al. | |
| 2006/0229689 A1 | 10/2006 | Ferguson et al. | |
| 2010/0174222 A1 | 7/2010 | McDaniel | |

OTHER PUBLICATIONS

Diffey BL (1980). "Ultraviolet radiation physics and the skin", Phys. Med. Biol. 25 (3): 405-426.

(Continued)

*Primary Examiner* — Gary Jackson
*Assistant Examiner* — Scott T Luan
(74) *Attorney, Agent, or Firm* — Dennis F. Armijo

(57) ABSTRACT

Illumination of the skin by substantial, monochromatic light emitted by LEDs, produces positive therapeutic effects for the treatment of a wide variety of skin conditions. Arrays of LEDs comprising multiple emission colors are preferred light sources for these applications, however, achieving uniform and efficient illumination of a skin target area in close proximity is difficult due to the point-like emission and narrow divergence of lensed LEDs. An illumination apparatus and method, provides a LED system that produces uniform and efficient illumination by combining a well-distributed computed arrangement of each of the LED colors on the array, to enhance the spatial overlap of individual LED outputs across the target area with a diffuse secondary reflector between the LEDs having high reflectivity to further enhance illumination uniformity by allowing light to bounce between LED array panels and the skin.

21 Claims, 12 Drawing Sheets

(56) References Cited

OTHER PUBLICATIONS

Papageorgiou P, Katsambas A, Chu A (2002). "Phototherapy with blue (415 nm) and red (660 nm) light in the treatment of acne vulgaris". Brit. J. Dermat. 142(5):973-978.

Adauwiyah J, Suraiya HH (Dec. 2010). "A retrospective study of narrowband-UVB phototherapy for treatment of vitiligo in Malaysian patients". Med. J. Malaysia 65(4): 297-9.

Kabat-Zinn J, Wheeler E, Light T, Skillings A, Scharf MJ, Cropley TG, Hosmer D, Bernhard JD (1998). "Influence of a Mindfulness Meditation-Based Stress Reduction Intervention on Rates of Skin Clearing in Patients With Moderate to Severe Psoriasis Undergoing Phototherapy (UVB) and Photochemotherapy (PUVA)". Psychosom. Med. 60:625-632.

Sutterfield R (Jan.-Feb. 2008). "Light therapy and advanced wound care for a neuropathic plantar ulcer on a Charcot foot". J Wound Ostomy Continence Nurs 35(1): 113-115.

Newman TB, Kuzniewicz MW, Liljestrand P, Wi S, McCulloch C, Escobar GJ (May 2009). "Numbers needed to treat with phototherapy according to American Academy of Pediatrics guidelines". Pediatrics 123 (5): 1352-9.

Lee SY, Park KH, Choi JW, Kwon JK, Lee DR, Shin MS, Lee JS, You CE, Park MY (2007). "A prospective, randomized, placebo-controlled, double-blinded, and split-face clinical study on LED phototherapy for skin rejuvenation: Clinical, profilometric, histologic, ultrastructural, and biochemical evaluations and comparison of three different treatment settings". J. Photochem and Phtobio. B: Biology 88(1):51-67.

Cavalcanti de Sousa AP, Santos JN, dos Reis Jr. JA, Ramos TA, de SOusa J, Cangussu MCT, Pinheiro ALB (2010). "Effect of LED Phototherapy of Three Distinct Wavelengths on Fibroblasts on Wound Healing: A Histological Study in a Rodent Model". Photomed. and Laser Surgery 28(4):547-552.

MULTICOLOR LIGHT EMITTING DIODE TREATMENT SYSTEM WITH UNIFORM ILLUMINATION

BACKGROUND OF THE INVENTION

Field of the Invention (Technical Field)

The presently claimed invention relates to phototherapeutic treatment and more particularly to an apparatus, system, and method for phototherapeutic treatment of skin conditions and mood/sleep related disorders using light emitting diodes (LEDs).

Background Art

Exposure of the skin to lights having specific colors in the ultraviolet, visible, and/or near-infrared spectral ranges is a proven method for the treatment of a wide range of conditions. This method, also known as phototherapy, is being used successfully for treating skin conditions such as psoriasis as described in *Ultraviolet Radiation Physics and the Skin*, Diffey B L, Phys. Med. Biol. vol. 25 (3), pp. 405-426 (1980), acne vulgaris as described in *Phototherapy with Blue (415 nm) and Red (660 nm) Light in the Treatment of Acne Vulgaris*, Papageorgiou P, Katsambas A, Chu A, British Journal of Dermatology, vol. 142(5), pp. 973-978 (2002) (hereinafter Papageorgiou), vitiligo as described in *A Retrospective Study of Narrowband-UVB Phototherapy for Treatment of Vitiligo in Malaysian Patients*, Adauwiyah J, Suraiya H H, Med. J. Malaysia 65(4), pp. 297-299 (December 2010), as well as treating various seasonal affective disorders as described in *Influence of a Mindfulness Meditation-Based Stress Reduction Intervention on Rates of Skin Clearing in Patients With Moderate to Severe Psoriasis Undergoing and Phototherapy (UVB) and Photochemotherapy (PUVA)*, Kabat-Zinn J, Wheeler E, Light T, Skillings A, Scharf M J, Cropley T G, Hosmer D, Bernhard J D, Psychosom. Med., vol. 60, pp. 625-632 (1998). Phototherapy is often indicated for the treatment of neonatal jaundice as disclosed in *Numbers Needed to Treat with Phototherapy According to American Academy of Pediatrics Guidelines*, Newman T B, Kuzniewicz M W, Liljestrand P, Wi S, McCulloch C, Escobar, G J Pediatrics, vol. 23 (5), pp. 1352-1359 (May 2009) and in supporting wound healing as described in *Light Therapy and Advanced Wound Care for a Neuropathic Plantar Ulcer on a Charcot Foot*, Sutterfield R, J Wound Ostomy Continence Nurs., vol. 35(1), pp. 113-115 (January-February 2008). Phototherapy has also been shown to be beneficial for reducing undesired pigmentation as disclosed in U.S. Pat. No. 6,991,644, entitled Method and System for Controlled Spatially-Selected Epidermal Pigmentation Phototherapy with UVA Leds, to Spooner, et al., (Jan. 31, 2006), and supporting skin rejuvenation by increasing the amounts of collagen and elastic fibers, as described in *A Prospective, Randomized, Placebo-Controlled, Double-Blinded, and Split-Face Clinical Study on LED Phototherapy for Skin Rejuvenation: Clinical, Profilometric, Histologic, Ultrastructural, and Biochemical Evaluations and Comparison of Three Different Treatment Settings*, Lee S Y, Park K H, Choi J W, Kwon J K, Lee D R, Shin M S, Lee J S, You C E, Park M Y, J. Photochem and Phtobio. B: Biology, vol. 88(1), pp. 51-67 (2007), hereinafter (Lee).

Specific colors of light are particularly effective for treating certain conditions. For example, light having primary wavelengths of 633 nm (red) and 830 nm (near-infrared) is effective for collagen and elastic fiber production in skin rejuvenation, as discussed in Lee. Light of 700 nm (near-infrared) and 530 nm (green) wavelengths can increase fibroblasts for accelerated wound healing as described in *Effect of LED Phototherapy of Three Distinct Wavelengths on Fibroblasts on Wound Healing: A Histological Study in a Rodent Model*, Cavalcanti de Sousa A P, Santos J N, dos Reis Jr. J A, Ramos T A, de Sousa J, Cangussu M C T, Pinheiro A L B, Photomed and Laser Surgery, vol. 28(4), pp. 547-552 (2010) and light of 415 nm (blue) and 660 nm (red) is effective in supporting the treatment of acne vulgaris as discussed in Papageorgiou.

LEDs are a cost-effective means of producing the desired wavelengths, the relatively narrow spectral power distributions, and the relatively low optical power levels desired for phototherapy. A phototherapy device incorporating a plurality of LEDs with different colors is particularly attractive and can be used for the treatment of multiple conditions. Uniform illumination of the skin is essential for the treatment of skin conditions to ensure an unvarying stimulation of the treatment area. Furthermore, the light emitted by the LEDs should reach the treatment area in order to maximize the illumination efficiency, thus, allowing the use of fewer and/or lower-power LEDs.

LEDs are incoherent light sources that emit light with a wide angular (Lambertian) distribution compared to lasers that emit a narrow beam of light. Lenses (primary optics) are often directly integrated with the LED chip into a single package in order to redirect most of the LED chip light output into a relatively narrow cone in the forward direction.

Ideally, an LED phototherapy device uses all the emitted light to illuminate the subject's skin treatment area in a uniform manner. In order for the device to be cost-effective and produce a high quality light for phototherapeutic applications, both high illumination uniformity and high illumination efficiency are necessary. However, these two properties tend to be mutually exclusive because of the inherent divergence of the LED output. For example, at a substantial distance between an LED array and a subject (e.g. >0.5 foot), the illumination uniformity is generally high because the diverging light output of the individual LEDs overlap. However, the efficiency is low because much of the emitted light misses the subject's treatment area. In contrast, the illumination efficiency is high at a close distance (e.g. <0.5 foot) where the LED array is "near the skin" of the subject; in this case, the illumination is non-uniform because of reduced overlap of the diverging LED outputs.

Non-uniform illumination of the skin treatment area is not desirable. However, when using LEDs with different colors and intensities arranged on a panel, it is difficult to obtain a uniform illumination of a given treatment area in close proximity. This is because lensed LEDs are substantially point-like light sources that typically emit light into a relatively narrow forward cone. Yet close proximity of the LED array to the skin is preferable in order to make best use of the emitted light (high illumination efficiency).

FIGS. 1A through 1F illustrate the problem. These figures represent the calculated illumination of a fixed-area target surface placed parallel to a LED array at different distances. The representative arrangement in this example comprises 22 LEDs with a divergence of ±15° and placed on a 10×7 rectangular grid with a LED spacing of 17.8 mm and 21.5 mm in the horizontal and vertical directions, respectively. FIG. 1A shows the efficiency of 99.0% at 1 inch, FIG. 1B shows the efficiency of 90.0% at 3 inches, FIG. 1C shows the efficiency of 79.5% at 6 inches, FIG. 1D shows the efficiency of 62.0% at 12 inches, FIG. 1 E shows the efficiency of 39.7% at 24 inches, and FIG. 1F shows the efficiency of 21.8% at 48 inches. For example, the spatial intensity distribution on a target surface (fixed area) in close proximity (1 inch) and parallel to a planar array of LEDs is highly non-uniform (FIG. 1A). Moving the target surface away from the LED array (FIGS. 1B-F) improves the spatial intensity distribution due to the greater spatial overlap of the diverging LED outputs; however, it comes at the expense of a reduced irradiance of the target surface as much of the light misses the target surface due to divergence. Space constraints further exacerbate the problem when an array of LEDs with several different colors is used and uniform illumination of the target area for each of those colors is preferable. Given a certain number of LEDs, the challenge is to find an LED arrangement and device design that gives both high illumination uniformity and high illumination efficiency.

Existing systems have the LEDs in rows or arranged for ease of manufacturing, but not based on optimal performance for the skin. Some systems require the user to move the device across the skin manually in an attempt to illuminate, uniformly all portions of the treatment area. Other devices require the user to lay stationary and move the LED panel to achieve uniform illumination; and still other devices use a large number of LEDs with the subject at a significant distance to achieve uniform illumination. These complexities and associated costs often limit existing devices to only one or two colors.

Several prior art approaches (and combinations of those) have been used in an attempt to solve the problem of achieving uniform and efficient illumination of a subject's skin.

Some devices are intended for use at a relatively large distance between the LED panel and the subject. At the large distance, the outputs of the individual LEDs mix well and produce a favorable, uniform illumination. An example of this approach is a LED panel described in U.S. Pat. No. 6,896,693 that is intended to be used at distances greater than 6 inches and up to several feet.

Other devices use a linear array of LEDs mounted in rows on an arm structure that moves back and forth on a semicircle with the subject stationary at the center of the arc. This can be combined with a relatively large distance (>6 inches) between the LEDs and the subject. The motion of the LEDs relative to the stationary subject and the distance creates a substantially uniform illumination of the subject's skin. An example is the MAX device marketed by MAX LED Technologies (Montreal, Quebec; http://www.maxledtechnologies.com). Another example are small handheld LED devices that have to be moved around the subject's skin like the ones marketed by Sirius Beauty (http://www.siriusbeauty.com), Bright Therapy (http://brighttherapy.com/acne-lamp-led-green-red-blue-infrared-led-cluster-with-3-detachable-treatment-heads.html), LightStim (http://www.lightstim.com), and many others. It is time consuming and tiring to use a small handheld device to cover large areas of the body, thus, making it less likely to sustain consistent use by the consumer.

Some devices use a large number of LEDs of a single color in the panel. Increasing the number of LEDs increases the spatial overlap of their outputs and produces a substantially uniform illumination. An example is the device marketed by Omnilux (http://www.omnilux.co.uk).

Other devices use secondary optics such as light guides and transmissive diffusers placed between the LED sources and the target area in order to achieve a substantially uniform illumination. Examples are U.S. Pat. Nos. 7,077,544 and 5,876,107 in which a transparent member (light guide) is used in conjunction with a LED source. Another example is a device marketed by Beauty Essence Co. that uses intricate mirror-like reflectors around each LED (http://www.amazon.com/Charming-Foldable-Machine-Rejuvenation-Dynamic/dp/B008X0WEUI/ref=sr_1_1?s=hpc&ie=UTF8&qid=1398647823&sr=1-1).

Some devices use a non-uniform spatial distribution of the LEDs in an array, optionally combined with individually adjusted LED intensities to achieve a substantially uniform illumination of a target surface. An example is U.S. Pat. No. 7,131,990.

In general, the above prior art approaches have a small treatment area and/or only a few (typically 1 or 2) colors. Most systems have non-uniform illumination, and some have complex moving parts. All these disadvantages make these devices less user-friendly and effective for the consumer.

The specific drawbacks of the above-described approaches are:

Relatively large distance: The drawback is that much of the emitted, highly divergent light does not reach the subject's skin and the irradiance is low, resulting in reduced phototherapeutic effects.

Motion of the LEDs: The disadvantage is that the device is larger and more complex/costly (compared to a device with stationary LEDs) because of the motion apparatus. In addition, the relatively large distance between the LEDs and the subject reduces the effective irradiance.

Large number of LEDs: The disadvantage is that the large number of LEDs comes at increased cost and power consumption. Furthermore, such devices often use only one or two therapeutic colors due to space/cost constraints.

Secondary optics: The disadvantage is that the added optical elements can make the device bulky, heavier, less efficient, and more expensive.

Non-uniform spatial distribution of the LEDs: There are infinite numbers of possibilities to arrange LEDs non-uniformly on a panel. Different arrangements produce different degrees of illumination uniformity. Non-uniform arrangement of LEDs is an effective way to achieve uniform illumination, and it is used in the presently claimed invention; however, the LED arrangement is paramount to the efficiency of the system.

Several units provide LED light therapy to the consumer, but in various other forms. Some are small, round or triangular shaped heads containing ~30 LEDs integrated into a handle; others are panels that contain one or two colors in various configurations; even others, as a bendable pad or a single panel. None achieves substantial, uniform illumination for four colors.

While arrangements of LEDs on arrays that achieve uniform illumination of a target area have been described, those arrangements typically follow simple and often symmetric patterns (such as alternating two colors on a grid). With multiple colors of LEDs having different light intensities for each color and a given number of LEDs in each color (to achieve the desired overall optical power level in each color), especially for three or more colors, it is not obvious how to best arrange the LEDs so that each emission color achieves the best possible illumination uniformity and illumination efficiency of a target surface. The computational method disclosed herein is an efficient way to identify LED arrangements that offer the desired properties. A given light intensity per color can be obtained for any number of colors with optimized light output uniformity on a given target.

Therefore, there is a need for a LED phototherapy device that has a plurality of colors, achieves a substantially uniform illumination for each color over a treatment area in close proximity without the need for moving the device, and is cost effective.

SUMMARY OF THE INVENTION

Disclosure of the Invention

The presently claimed invention overcomes the shortcomings of the prior art by providing a multi-color LED panel that produces a substantially uniform illumination for each of the LED colors individually, on a subject in close proximity (<0.5 foot) without the need for using secondary optics or moving the LED panel. Specifically, the claimed LED invention comprises four emission colors that produce high illumination uniformity and high illumination efficiency of a large treatment area in close proximity (<0.5 foot). A four-color device, comprising blue (~452 nm), yellow (~592 nm), red (~642 nm), and near-infrared (~838 nm) LEDs, achieves a synergistic effect in the skin producing better outcomes for the consumer.

The presently claimed invention achieves superior performance, especially in close proximity, using a combination of three design elements:
- the hinged three-panel design allows the face and neck treatment area to be intimately enveloped by the LED light source;
- the LEDs on each panel are arranged in order to achieve optimal emission from each color across the entire panel to produce effective spatial overlap of the LED outputs, and;
- the space between the LEDs on the panel is covered with a diffuse reflector having high reflectance (white color), allowing light to bounce back and forth between panels and the skin in order to enhance the illumination uniformity.

The large panels emitting four colors and illuminating the target area uniformly in close proximity, allow high-performance illumination of the entire face/neck area. The four colors offer a synergistic effect that when combined with the high illumination uniformity, produces better therapeutic results compared to traditional devices.

Furthermore, the use of surface-mount LEDs allows for a thinner, lighter, system that is more convenient to use and cheaper to manufacture. The space between the surface-mount LEDs is utilized to place the circuitry for the LED drivers, allowing the drivers and associated heat load to be spread out across the panel. Existing devices use traditional through-hole LEDs (bulky and expensive to assemble) rather than miniature surface-mount LEDs (compact and cost-effective assembly).

One advantage of the presently claimed invention is that it provides substantially uniform and efficient illumination with light from an LED array of a target area in close proximity. Another advantage of the presently claimed invention is that the LED illumination is successful over a substantial target area, offering phototherapeutic treatment of the patient's face and neck area without the need for moving the device.

A further advantage of the presently claimed invention is that it provides illumination of the target area with LED light having multiple colors in order to achieve multiple and/or synergistic phototherapeutic effects. Yet another advantage of the presently claimed invention is that it achieves this high-quality LED illumination with a limited number of LEDs, thereby enabling a cost-effective and compact device.

Other objects, advantages, and novel features, along with a further scope of applicability of the presently claimed invention will be set forth in part in the detailed description to follow. In conjunction with the accompanying drawings, the presently claimed invention will become apparent to those skilled in the art who examine the following, or learned by practice of the presently claimed invention.

The objects and advantages of the presently claimed invention may be understood and achieved by utilizing the instrumentalities and combinations thereof, and by indication of the appended claims.

BRIEF DESCRIPTION OF THE DRAWINGS

The accompanying drawings, which are incorporated into and form a part of the specification, illustrate several embodiments of the presently claimed invention and, together with the description, serve to explain the principles of the presently claimed invention. The drawings are only for the purpose of illustrating a preferred embodiment of the claimed invention and are not to be construed as limiting the claimed invention. In the drawings:

DESCRIPTION OF THE PREFERRED EMBODIMENTS

Best Modes for Carrying Out the Invention

The presently claimed invention relates to the design and implementation of an LED device for the phototherapeutic treatment of skin. Further, the embodiments disclosed herein achieve efficient and uniform illumination of the face and neck areas of a person positioned in close proximity to the LED light source.

Figure 1A:
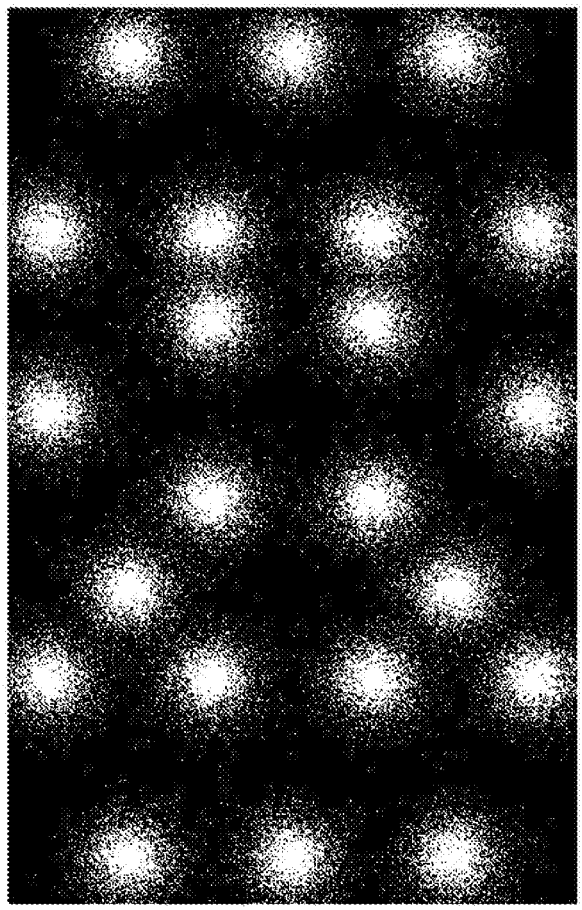
FIG. 1A represents the calculated illumination of a fixed-area target surface placed parallel to a LED array at 1 inch.
Figure 1B:
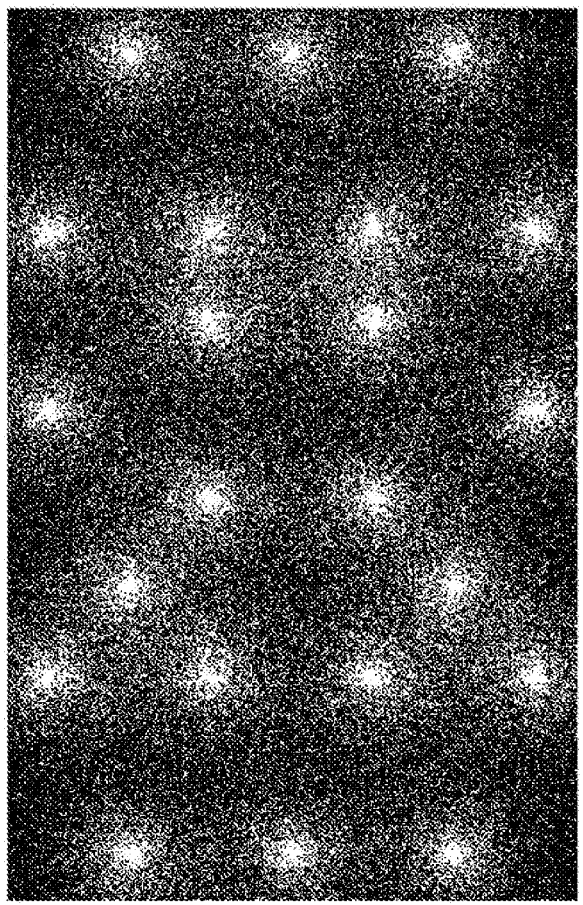
FIG. 1B represents the calculated illumination of a fixed-area target surface placed parallel to a LED array at 3 inches.
Figure 1C:
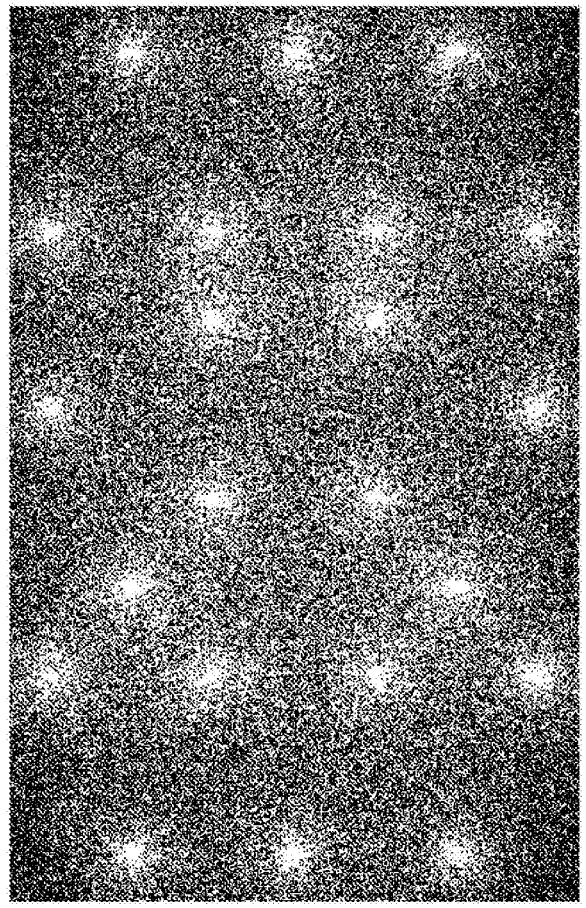
FIG. 1C represents the calculated illumination of a fixed-area target surface placed parallel to a LED array at 6 inches.
Figure 1D:
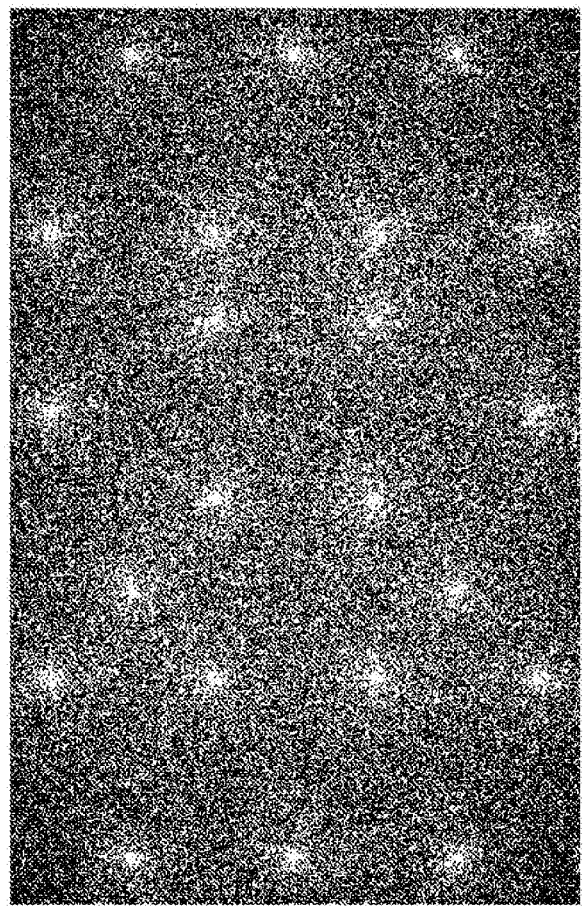
FIG. 1D represents the calculated illumination of a fixed-area target surface placed parallel to a LED array at 12 inches.
Figure 1E:
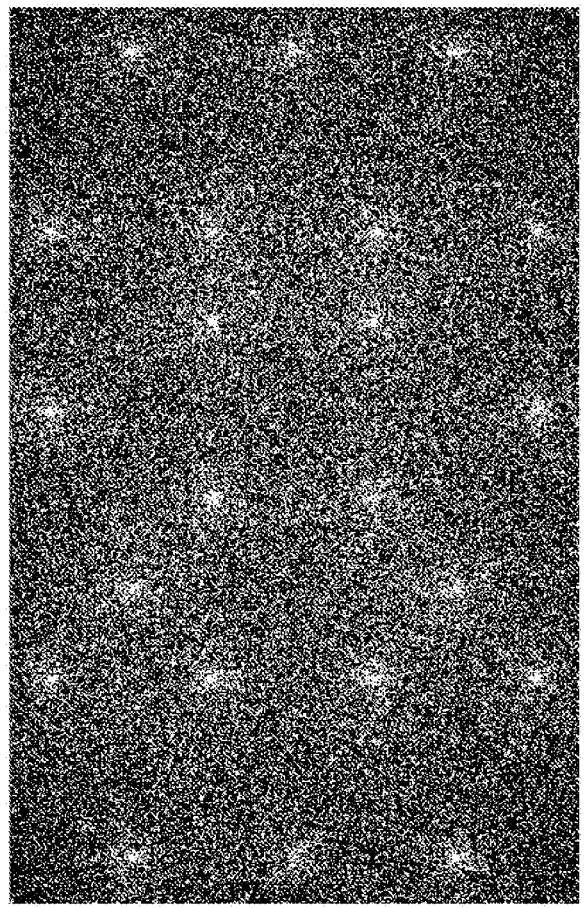
FIG. 1E represents the calculated illumination of a fixed-area target surface placed parallel to a LED array at 24 inches.
Figure 1F:
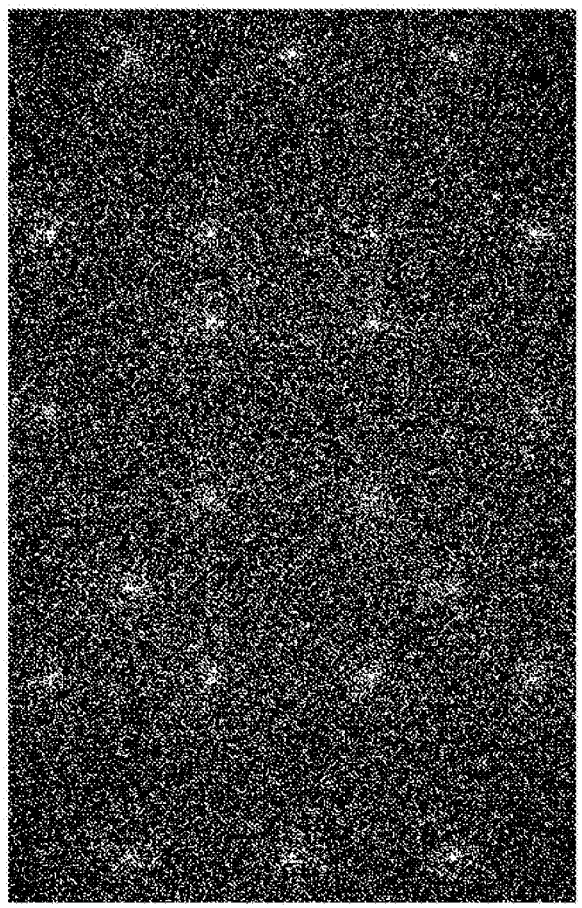
FIG. 1F represents the calculated illumination of a fixed-area target surface placed parallel to a LED array at 48 inches.
Figure 2A:
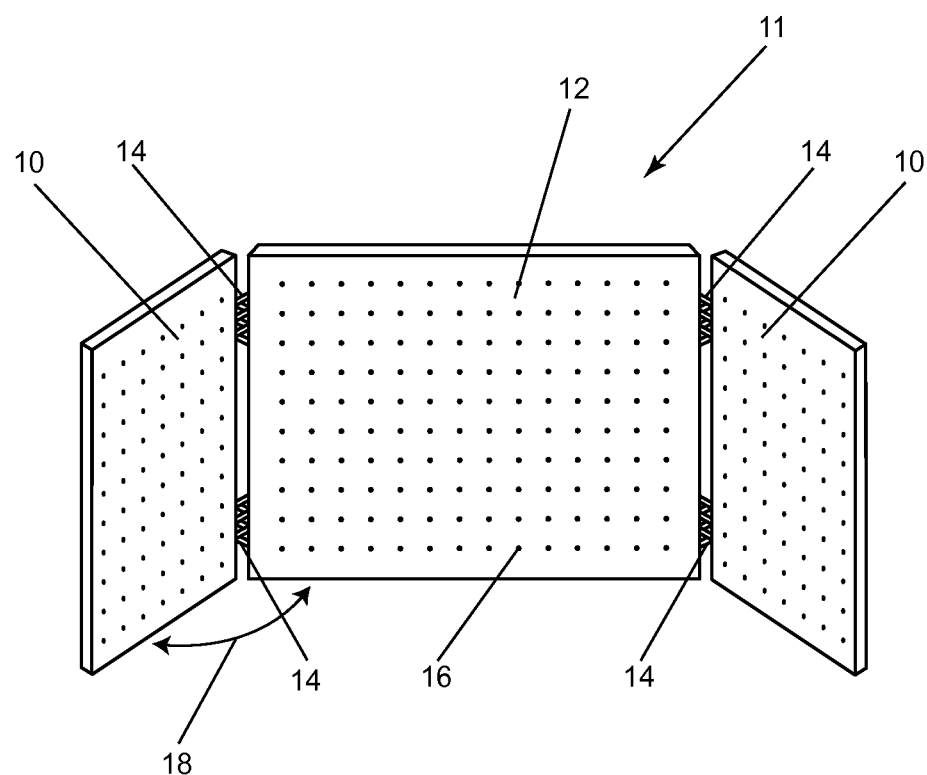
FIG. 2A shows the preferred embodiment of the illumination apparatus in an open configuration.
Figure 2B:
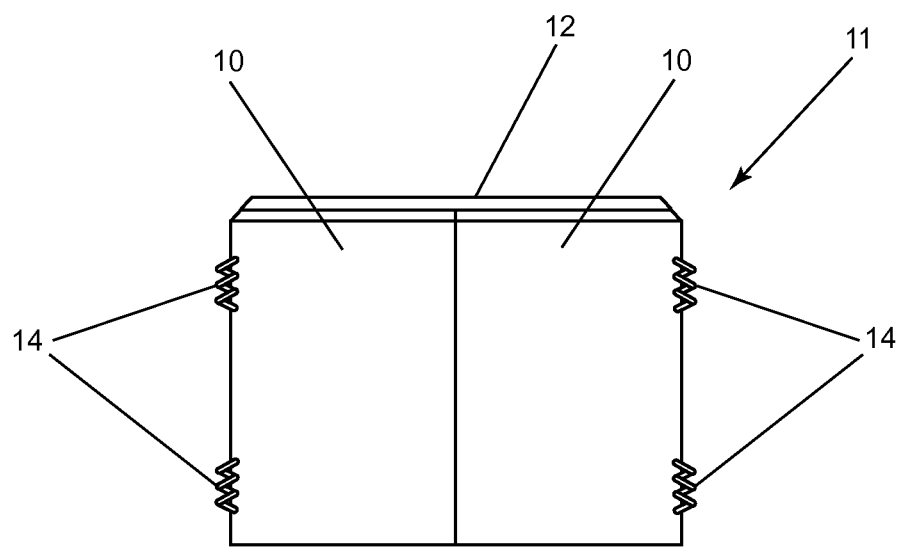
FIG. 2B shows the embodiment of FIG. 2A in a closed configuration.

The preferred illumination apparatus 11 consists of three panels. In the preferred embodiment, as shown in FIG. 2A, two side panels 10' and 10" (collectively referred to as 10) can fold over center panel 12 by means of hinges 14 to allow for a desirably thin form factor when the device is closed and not in use as shown in FIG. 2B. Center panel 12 preferably comprises a surface area and a configuration and number of mounted LEDs of two side panels. Each panel comprises multiple LEDs 16, and each has one of multiple emission colors. In the preferred embodiment, the width of each side panel 10' and 10" is approximately half the width of center panel 12 to allow complete folding of illumination apparatus 11 when in the closed position for storage (FIG. 2B).

Figure 3:
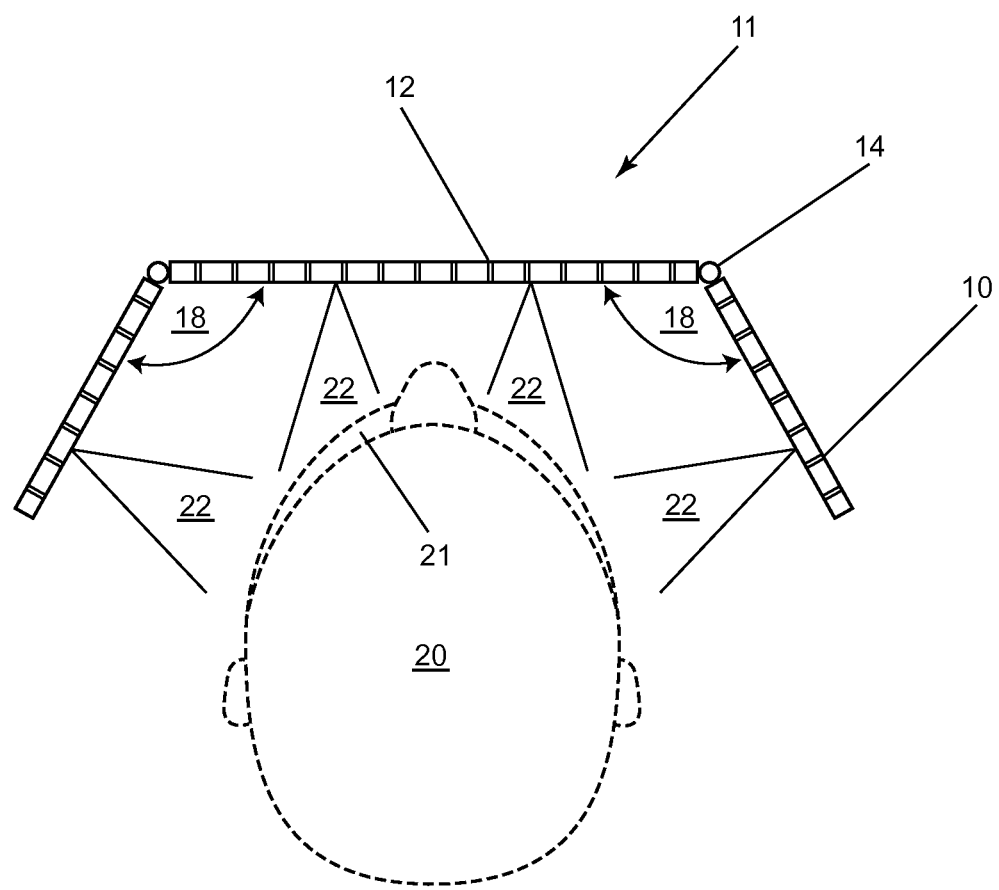
FIG. 3 shows the preferred method of using the illumination apparatus.

When in use, side panels 10 open to an angle 18 greater than 90° and less than 180°, as shown in FIG. 2A. In this position, and with proper dimensioning of the panels 10 and 12, the face and neck areas (target area) of a person 20 are substantially enveloped by the LED panels 10 and 12, as shown in FIG. 3. In this configuration, the front and sides of the patient's face and neck are illuminated efficiently by the diverging LED outputs 22.

Each panel 10 and 12 comprises a plurality of LEDs 16 each having one of several emission colors. The total number of LEDs 16 as well as the number of LEDs 16 for each color depends on the desired optical power level in each color and the optical performance specifications of each LED. In a preferred embodiment, shown in FIG. 4, a side panel 10 contains 32 blue LEDs 24 having a peak emission wavelength of 452±10 nm (part #SMT450-23 manufactured by Marubeni Corporation), 10 yellow LEDs 26 having a peak emission wavelength of 592±10 nm (part #LY-E63B-CBEA-26-1-Z manufactured by OSRAM Opto Semiconductors Inc.), 22 red LEDs 28 having a peak emission wavelength of 642±10 nm (part #LS-E63B-BBCB-1-1-Z manufactured by OSRAM Opto Semiconductors Inc.), and 6 near-infrared LEDs 30 having a peak emission wavelength of 838±10 nm (part #VSMG2700-GS08 manufactured by Vishay Semiconductor Opto Division). Although specific LEDs have been described in this disclosure, any other types and emission colors of LEDs are understood to be included in this document. Center panel 12 having twice the width of a side panel 10 can be formed, for example, by placing two side panels directly adjacent to each other.

Proper placement of the individual LED colors onto the positions of the array is essential for obtaining a high degree of illumination uniformity. Given a certain number of LEDs for each color, desired arrangements can be found by an iterative computational method that includes the steps of first generating a random arrangement of said LEDs on the array, calculating the weighted sum of the distances between each LED of a given color, and adding the sum of said distances to obtain a figure of merit for the particular arrangement. Second, two LEDs in the array are randomly chosen, their places are switched, and said figure of merit is calculated again. The new arrangement is adopted if the figure of merit has improved (increased); otherwise, the method reverts to the previous arrangement. The random switching of two LEDs is continued until no further improvement of the figure of merit is achieved. Third, the entire above process is repeated to find another LED arrangement with a high figure of merit, until no further improvement is achieved and a LED arrangement with the overall best figure of merit is obtained. This method of arranging and placing of the individual LEDs is referred to and defined herein as optimal LED placement methodology.

Figure 4:
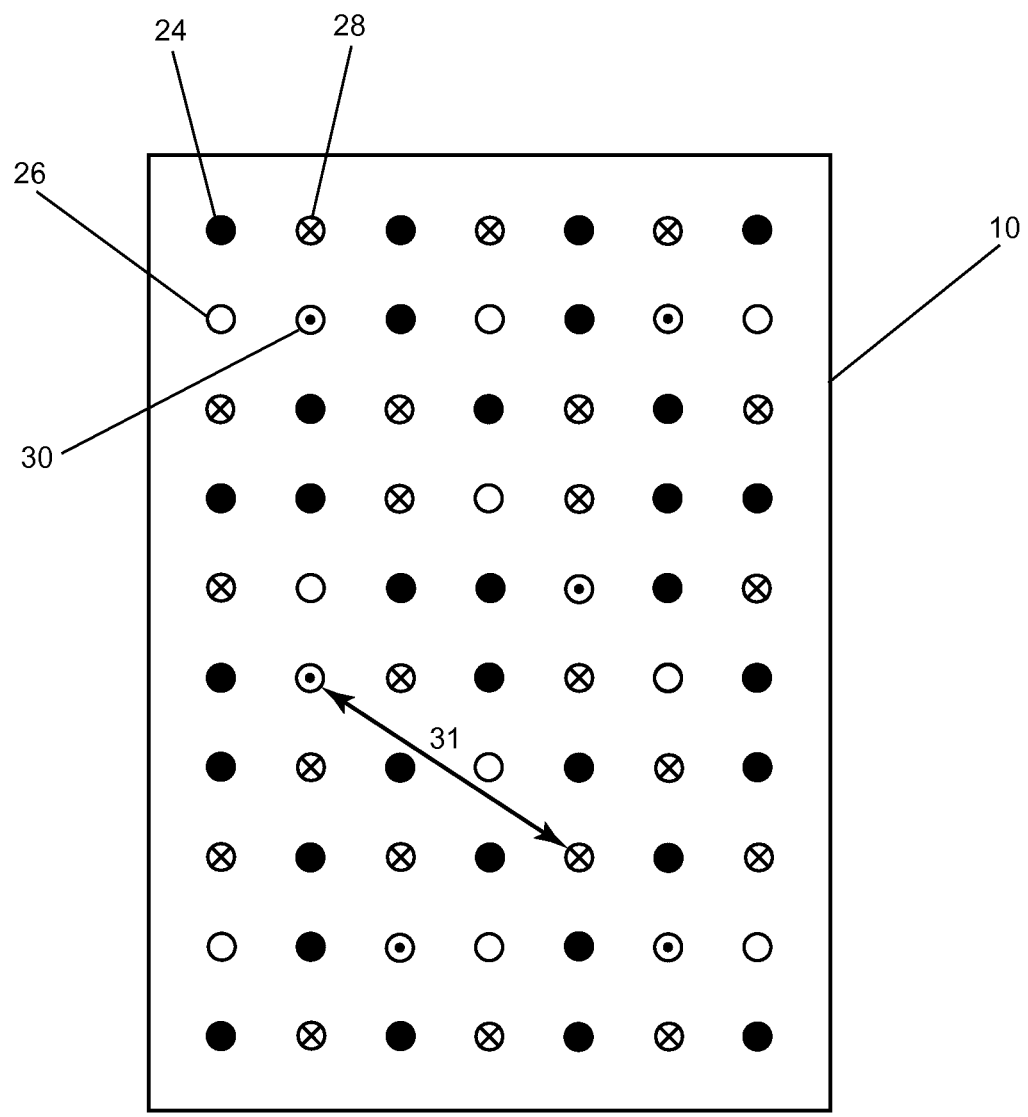
FIG. 4 shows a preferred configuration of the LED placement on a single panel.

FIG. 4 shows one preferred LED arrangement of 32 blue 24, 10 yellow 26, 22 red 28, and 6 near-infrared 30 LEDs on a 7-by-10 array geometry having cubic symmetry. It is readily recognized that there are numerous arrangements of LEDs for this array size that have substantially similar figures of merit. The arrangement shown in FIG. 4 is solely meant to illustrate a preferred arrangement, but a person skilled in the art will appreciate that other array geometries and/or other array symmetries (cubic, trigonal, tetragonal, hexagonal, orthorhombic, monoclinic, triclinic, etc.) and/or other LED numbers and color distributions are possible and equally benefit from using above computational method. The computational method ensures that the LEDs of each color are well distributed across the array in order to produce the desired high illumination uniformity of a target area 21 in close proximity. The task of identifying a favorable arrangement of LEDs on a given array geometry becomes increasingly difficult as the number of colors in the array increases. Therefore in a preferred embodiment, there is disclosed LED arrays comprising four emission colors and achieving high illumination uniformity of a target surface placed in close proximity.

Figure 7:
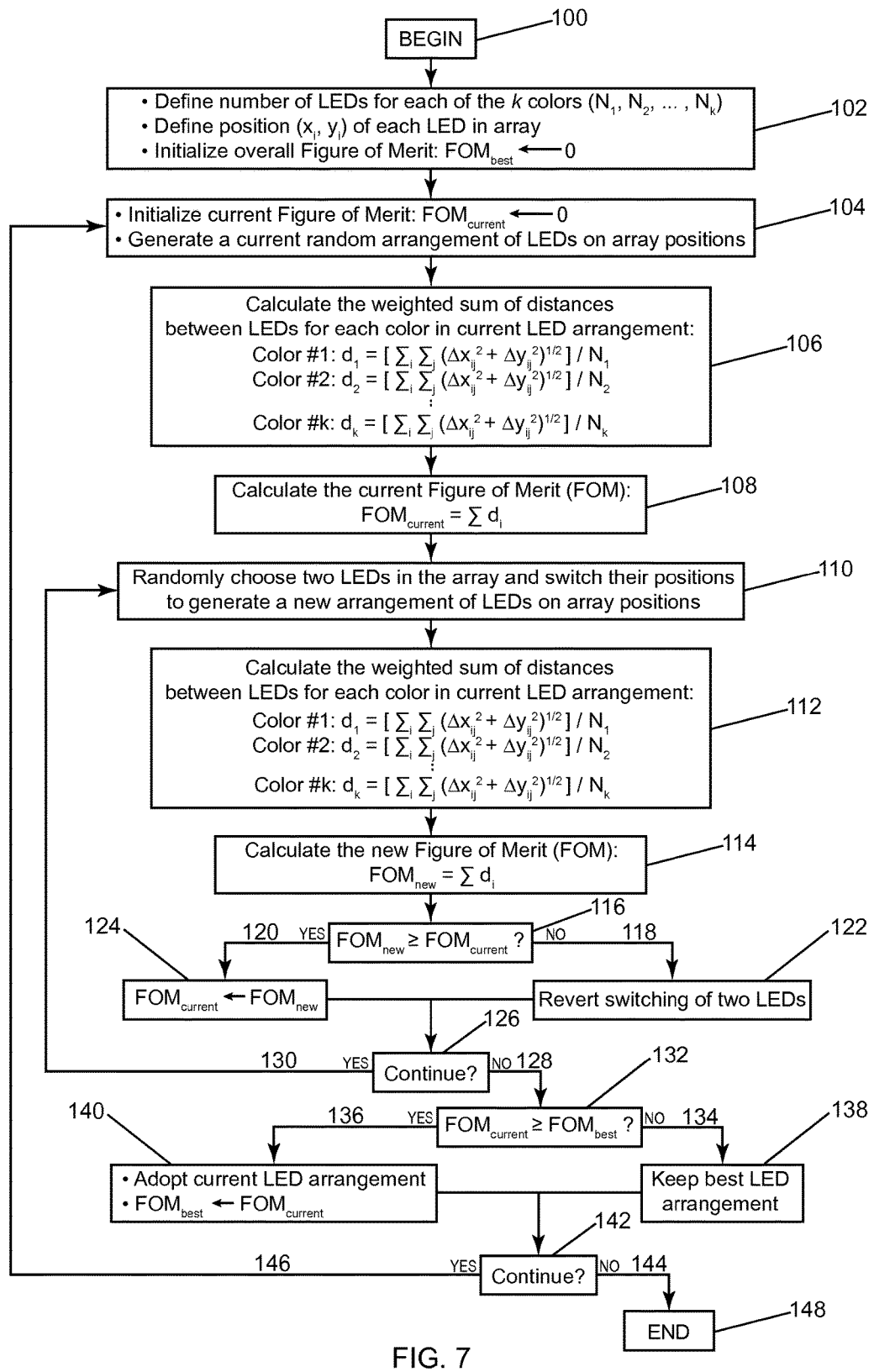
FIG. 7 is a flow chart showing the preferred LED arrangement selection method.

FIG. 7 is a flowchart showing the preferred method for arranging the LEDs in an optimal configuration. FIG. 4 is an example of one preferred arrangement of LEDs using the method of FIG. 7. Referring to FIGS. 4 and 7 is an example of the optimal arrangement process which can be used for different array configurations and different numbers and colors of LEDs. The process begins 100 at step 102 with a selection of LEDs of predefined colors and a definition of the spatial coordinates of the LED positions, step 104 a random placement of the LEDs in an array and step 108 calculating a figure of merit from step 106 which provides for calculating a weighted sum of distances between LEDs of each color. In FIG. 4 a random distribution of 32 blue 24, 10 yellow 26, 22 red 28, and 6 near-infrared LEDs 30 among the 70 positions of the 7-by-10 array is selected. The sum of all distances between blue LEDs and dividing this sum by the number of blue LEDs is calculated; second, the sum of all distances between yellow LEDs and dividing this sum by the number of yellow LEDs is calculated; third, the sum of all distances between red LEDs and dividing this sum by the number of red LEDs is calculated; and fourth, the sum of all distances between near-infrared LEDs and dividing this sum by the number of near-infrared LEDs is calculated, as described in step 106. The figure of merit is then obtained by adding the aforementioned weighted blue, yellow, red, and near-infrared sums, as shown in step 108. Step 110 provides for randomly choosing two positions on the 7-by-10 array, the respective LEDs are switched 31, and the new figure of merit is calculated in step 114 from the weighted sum of distances between LEDs of each color in the new arrangement, as shown in step 112. If the figure of merit of the new LED arrangement in step 116 is greater (better) 120 than the figure of merit of the previous LED arrangement, then the new arrangement is adopted in step 124 as it provides a more uniform LED distribution and hence produces a more uniform illumination of target area 21. Otherwise, if the figure of merit is smaller (worse) 118 the previous LED arrangement is kept by reverting 122 the two LEDs that were switched in step 110. The process then continues as shown in step 126 if the figure of merit is not optimal 130 back to step 110 where two different randomly selected LEDs are switched. This process of randomly switching two LEDs is repeated until an LED arrangement is obtained from which no further improvement is achieved 128. This LED arrangement and its associated figure of merit may represent a local maximum rather than the global maximum in the optimization of the figure of merit, requiring the steps 104-128 to be repeated. Therefore, if the figure of merit of the current LED arrangement in step 132 is greater (better) 136 than the figure of merit of the overall best LED arrangement, then the current arrangement is adopted in step 140 as it provides a more uniform LED distribution and hence produces a more uniform illumination of target area 21. Otherwise, if the current figure of merit is smaller (worse) 134 the overall best LED arrangement is kept. The process then continues as shown in step 142 if the overall best figure of merit is not optimal 146 back to step 104 where a new random placement of the LEDs is generated. Otherwise, if the overall best figure of merit achieves no further improvement 144 then the optimization process ends 148. Referring to FIG. 4, the figure of merit of this one preferred arrangement of 32 blue 24, 10 yellow 26, 22 red 28, and 6 near-infrared LEDs 30 on a 7-by-10 array is calculated to be 308.101. For example, switching the two LEDs indicated by double-arrow 31 in FIG. 4 reduces the figure of merit to 306.866, i.e. it leads to a less uniform LED arrangement and hence a less uniform illumination of the target surface.

Figure 5A:
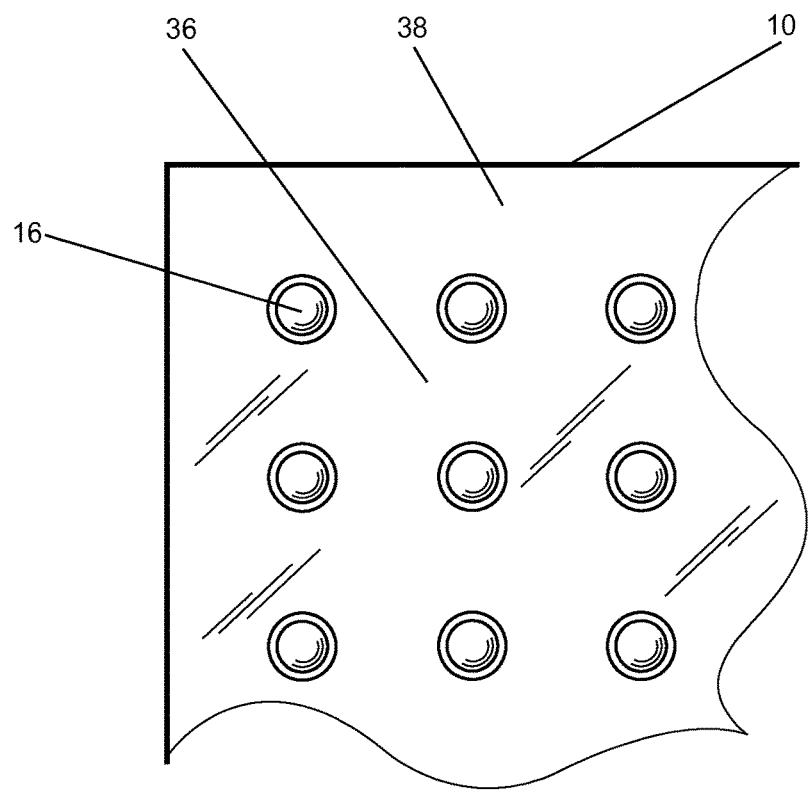
FIG. 5A shows a detailed view of a portion of the panel of FIG. 4.
Figure 5B:
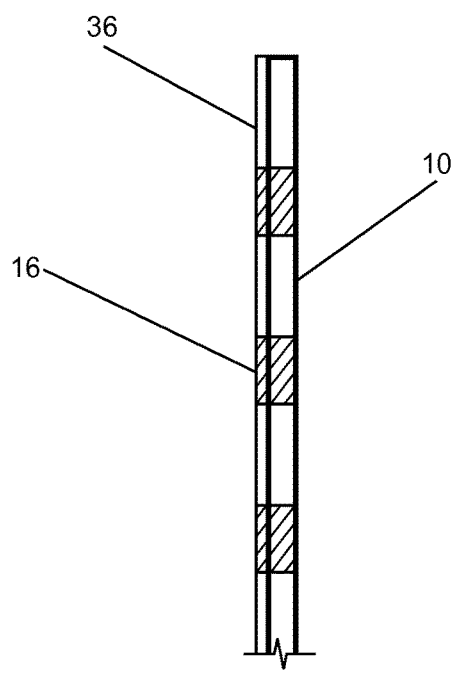
FIG. 5B shows a side view of FIG. 5A.
Figure 6:
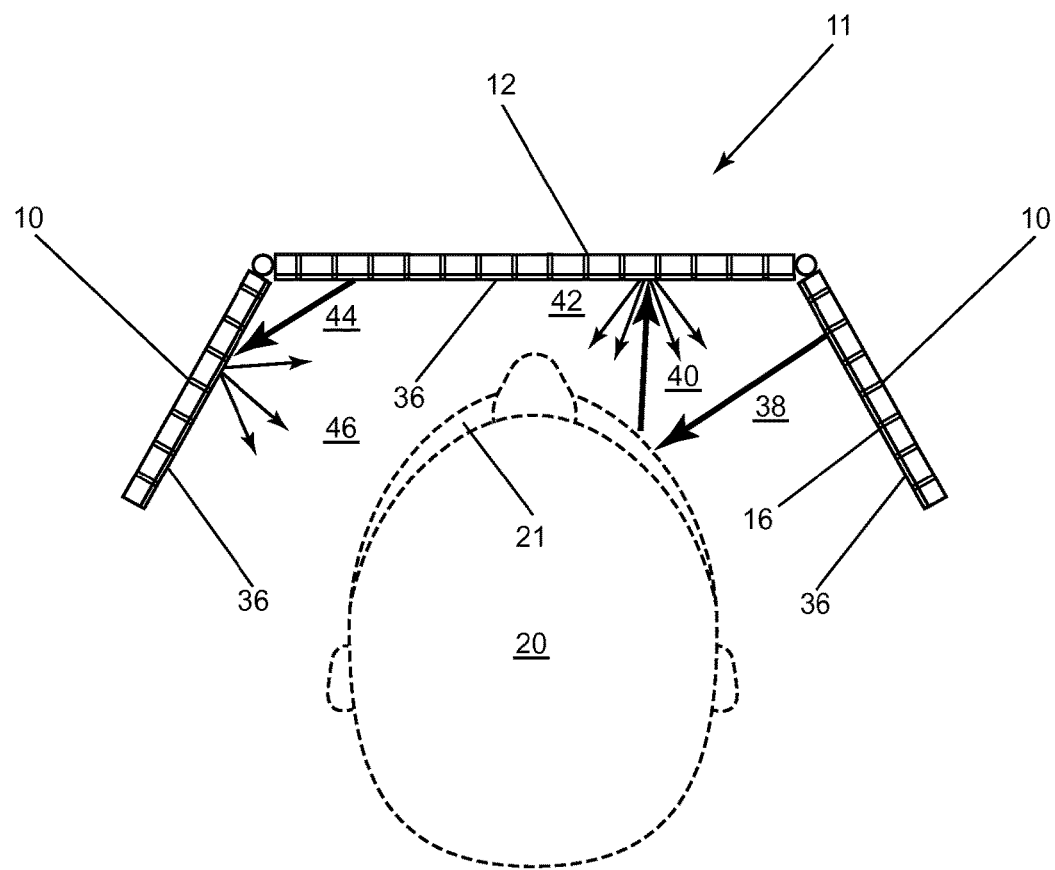
FIG. 6 illustrates the light emitted by the LEDs and being redirected using a diffuse reflector.

Another element of the innovation is illustrated in FIGS. 5A and 5B. LEDs 16 are arranged on a panel 10, and the area between the LEDs 16 is comprised of a material 36 that is an efficient diffuse reflector for the emission wavelengths of the LEDs that are present in the array. The purpose of diffuse reflector 36 is to redirect light propagating on rays that do not intersect with the target surface 21 back towards the target surface 21, as illustrated in FIG. 6. For example, light ray 38 originating from LED 16 on a side panel 10 strikes the skin of person 20. A fraction of the light will be absorbed by the skin to induce the desired phototherapeutic effect, while the remaining light will be scattered by and away from the skin as illustrated by light ray 40. Some of this light will strike diffuse reflector 36 and be redirected into light rays 42 that propagate back towards the target surface 21 on person 20. In a similar fashion, light ray 44 originating from LED 16 on one panel 12 can strike the diffuse reflector 36 on another panel 10' and be efficiently redirected into light rays 46 that propagate towards the target surface 21 on person 20. The aforementioned two light paths are examples chosen to illustrate the function of the diffuse reflector. It is recognized that a variety of light paths are possible for a geometry similar to that shown in FIG. 6. The overall effect of diffuse reflector 36 is to enable two benefits: First, repeated bouncing of light rays between LED panels 10, 12 as well as between LED panels 10, 12 and target surface 21 enhances the spatial overlap of the diverging LED outputs and therefore increases the illumination uniformity realized on target surface 21. Second, redirection of light propagating on rays that do not intersect with target surface 21 by diffuse reflector 36 enhances the illumination efficiency as light that would otherwise have been lost, is redirected towards target surface 21. Note that diffuse reflector 36 acts as a secondary reflector, that is, it reflects light that has previously left the surface of originating LED panel 10, 12. This is in contrast to primary transmissive diffusers, often used in existing devices and are placed in the light path between the LED source and the target area, requiring all light to pass through the diffuser. Using a secondary reflective diffuser instead of a primary transmissive diffuser achieves higher illumination efficiency because diffuser back reflection inherent to transmissive diffusers is eliminated in this novel configuration.

In some embodiments, it may be beneficial for diffuser 36 to extend into an area 38 beyond the area defined by the LED array such that the diffuser area is greater than the area defined by the LED array. In this manner, rays propagating at high angles with respect to the surface normal of panels 10, 12 or target surface 21 on paths that do not intersect with target surface 21 can be redirected back towards target surface 21.

The preferred diffuse reflector 36 can be made of a variety of materials and placed between the LEDs 16 in a variety of methods. For an array, comprising LEDs with several emission colors across the visible wavelength range (blue, yellow, red, or near-infrared LED array) diffuse reflector 36 material will generally have a white physical appearance to the human eye. The diffuse reflector 36 material has a rough surface so as to minimize specular reflection and favor diffuse reflection. Diffuse reflector 36 can be fabricated as a rigid or flexible sheet comprising apertures for accommodating the LEDs, and then mounted close to or directly on the LED array. The diffuse reflector can be made, for example, from GORE® Diffuse Reflector material manufactured by the Gore Company of Newark, Del. Alternatively, a white material can be applied to the area between the LEDs as a coating, spray paint, or similar layer. Such a coating can be obtained, for example, by applying a matte Ti-Pure® titanium dioxide pigment manufactured by the DuPont Company. A person skilled in the art will recognize that other materials and/or other methods of applying the diffuse reflector will similarly achieve the desired diffuse reflectance function. It is also not necessary for diffuse reflector 36 to be visually white to the human eye, as long as diffuse reflector 36 provides a high degree of reflectance for the substantially monochromatic emissions of LEDs 16 present in the array, which is possible in LED arrays comprising only one, two, or three LED emission colors. An LED array comprising only blue 24 and red emitting LEDs 28 might use a diffuse reflector 36 of purple appearance that has high reflectance for both blue 24 and red colors 28 while having lower reflectance for the green light present in ambient lighting. In this example, the absorption of ambient green light by diffuse reflector 36 material is irrelevant to the aforementioned function of the diffuse reflector 36 because only the blue 24 and red LED 28 emission colors are relevant for this particular device.

The preferred plurality of LEDs 16 produces the light required to achieve the desired phototherapeutic effect. The specific phototherapeutic effect achieved depends on the emission wavelength. Illumination apparatus 11 can therefore comprise identical LEDs of only one emission color in order to achieve one particular phototherapeutic effect. Alternatively, and more desired, a preferred illumination apparatus 11 incorporates a plurality of LEDs each having one of several emission wavelengths to achieve multiple treatment modalities and/or synergistic phototherapeutic effects. The arrangement of the LEDs on each panel determines the illumination uniformity and illumination efficiency of a target surface in close proximity. The LEDs are ideally arranged so that the sum of the distances between LEDs of the same color is maximized. Instead of using sets of different LEDs emitting specific colors, integrated multicolor LEDs could be used in order to allow emission of each of the colors from every LED in the array. This would improve the illumination uniformity, but would likely be more expensive. The wavelengths of the light emitted by the LEDs could be different from the ones described above. For example, green LEDs could be added, or alternatively other wavelengths for the blue LEDs could be used.

The preferred panels 10, 12 comprise a rigid or flexible surface with mounted LEDs that also contain electrical connections for powering the LEDs and possible other components such as LED driver circuitry, connectors, etc. In a preferred embodiment, panel 10, 12 comprising the LED array is a rigid planar printed circuit board, mounted inside a closely fitting enclosure. Thus, the panel serves both a mechanical and an electrical purpose. In addition, proper arrangement of multiple panels 10, 12 aids in enhancing the illumination uniformity and illumination efficiency. Specifically, a preferred embodiment consists of a center panel 12 and two hinged side panels 10 allowing substantial enveloping of the face and neck area of a human 20 undergoing phototherapy. The three-panel design achieves high illumination uniformity and illumination efficiency when the side panels 10 are each opened to an angle between 90° and 180° with respect to the center panel 12. Furthermore, a particular form-factor benefit is achieved when side panels 10 are approximately half the width of center panel 21, thereby allowing the illumination apparatus 11 to close into a substantially thin folded arrangement when the device is not in use, FIG. 2B. The panels could be made flexible by using a flex circuit board rather than a rigid circuit board to mount the LEDs in the array that enables a different means (compared to hinged rigid panels) of enveloping the patient's treatment area. Instead of using three hinged panels, a single panel could be used to enable a simpler and less expensive device, at the expense of illumination uniformity and illumination efficiency.

Alternative embodiments can include a mounting arm or stand, allowing the hinged three-panel device to be held in position during the duration of the treatment; a power supply and controller that supplies electrical power to the LED array and performs control functions such as timing the on/off time of the individual colors, light intensity, user notifications, etc.; and cables connecting the power supply to a wall plug as well as connecting the power supply/connector to the LED array (not shown).

Although the presently claimed invention has been described in detail with particular reference to these preferred embodiments, other embodiments can achieve the same results. Variations and modifications of the presently claimed invention will be obvious to those skilled in the art and are intended to cover all such modifications and equivalents. Incorporated herein by reference are the entire disclosures of all references, applications, patents, and publications cited above.

What is claimed is:

1. A method for arranging at least two colors of light emitting diodes (LEDs) for phototherapeutic treatment, the method comprising the steps of:
    a) selecting a first number of LEDs for a first emission color and at least one second number of LEDs for at least one next emission color;
    b) selecting a random arrangement of the first number and the at least one second number of LEDs for a set of locations;
    c) calculating a first weighted sum of distances between each LED of the first color;
    d) calculating at least one next weighted sum of distances between each LED of the at least one next color;
    e) obtaining a figure of merit by summing the first weighted sum with the at least one next weighted sum;
    f) switching a placement of two randomly selected LEDs;
    g) recalculating a new figure of merit;
    h) if the new figure of merit is increased, maintaining the placement, if the new figure of merit is decreased, reverting to an original placement of the two randomly selected LEDs;
    i) switching a next placement of two next randomly selected LEDs; and
    j) repeating steps c) through h) until no further increase on a next figure of merit is calculated.

2. The method of claim 1 further comprising the step of repeating steps b) through j) for a next set of locations until no further increase on a final figure of merit is calculated.

3. The method of claim 1 wherein the at least two colors of the LEDs comprise blue LEDs, yellow LEDs, red LEDs, and near-infrared LEDs.

4. The method of claim 3 wherein the blue LEDs comprise 32 blue LEDs, the yellow LEDs comprise 10 yellow LEDs, the red LEDs comprise 22 red LEDs and the near-infrared LEDs comprise 6 near-infrared LEDs.

5. The method of claim 1 wherein the arranging of at least two colors of LEDs comprises arranging the LEDs on a panel.

6. The method of claim 1 wherein the arranging comprises a grid having a member selected from the group consisting of cubic, trigonal, tetragonal, hexagonal, orthorhombic, monoclinic and triclinic symmetry.

7. A phototherapeutic apparatus comprising:
    at least one panel;
    a plurality of LEDs, the plurality of LEDs comprising a first set of LEDs comprising a first emission color and at least one second set of LEDs comprising at least one second emission color, wherein the plurality of LEDs are disposed on the at least one panel using a random arrangement of said LEDs, calculating the weighted sum of the distances between each LED of a given emission color, adding the sum of the distances to obtain a figure of merit for the random arrangement, switching a placement of two randomly selected LEDs and recalculating the weighted sum, and repeating a next switched placement of a next two randomly selected LEDs and a next recalculation until a maximum figure of merit is achieved for a set of locations; and
    a diffuse reflector disposed on the at least one panel between the plurality of LEDs.

8. The phototherapeutic apparatus of claim 7 wherein the at least one panel comprises a first side panel, two center panels adjacent to each other and a second side panel.

9. The phototherapeutic apparatus of claim 8 wherein the first side panel and second side panel are hinged to the two adjacent center panels.

10. The phototherapeutic apparatus of claim 7 wherein the at least one panel comprises a member from the group of array geometries consisting of cubic, trigonal, tetragonal, hexagonal, orthorhombic, monoclinic and triclinic.

11. The phototherapeutic apparatus of claim 7 wherein first emission color comprises blue and the at least one next emission color comprise yellow, red and near-infrared.

12. The phototherapeutic apparatus of claim 11 wherein the blue comprises 32 blue LEDs, the yellow comprises 10 yellow LEDs, the red comprises 22 red LEDS and the near-infrared comprises 6 near-infrared LEDs.

13. The phototherapeutic apparatus of claim 7 wherein the diffuse reflector comprises a material that redirects light propagating on rays that do not intersect with a target surface towards the target surface.

14. The phototherapeutic apparatus of claim 7 wherein the diffuse reflector comprises a rough surface.

15. The phototherapeutic apparatus of claim 7 wherein the diffuse reflector is affixed to the exterior surface of the at least on panel and further comprises an aperture for each LED of the plurality of LEDs.

16. The phototherapeutic apparatus of claim 7 wherein the diffuse reflector comprises a member from the group consisting of a sheet, a coating and a laminate.

17. The phototherapeutic apparatus of claim 7 wherein the diffuse reflector comprises a flexible diffuse reflector.

18. A method for providing phototherapeutic treatment to a target surface, the method comprising the steps of:
providing at least one panel comprising a plurality of LEDs, the plurality of LEDs comprising a first set of LEDs comprising a first emission color and at least one second set of LEDs comprising at least one second emission color, wherein the plurality of LEDs are disposed on the at least one panel using a random arrangement of the LEDs, calculating the weighted sum of the distances between each LED of a given emission color, adding the sum of the distances to obtain a figure of merit for the arrangement, switching a placement of two randomly selected LEDs and recalculating the weighted sum, and repeating a next switched placement of a next two randomly selected LEDs and a next recalculation until a maximum figure of merit is achieved for a set of locations;
setting the target surface to be substantially enveloped by the at least one panel; and
energizing the plurality of LEDs.

19. The method of claim 18 further comprising the step of opening a first side panel and a second side panel from the at least one panel to angles greater than 90° to 180° from a center panel.

20. The method of claim 18 wherein the step of energizing comprises energizing the LEDs in a sequence one emission color at a time.

21. The method of claim 18 further comprising the step of redirecting light propagating on rays that do not intersect with the target surface towards the target surface.

* * * * *